(12) United States Patent
Benning et al.

(10) Patent No.: US 10,750,934 B2
(45) Date of Patent: Aug. 25, 2020

(54) ENDOSCOPIC SYSTEM FOR OPTIMIZED VISUALIZATION

(71) Applicant: Boston Scientific Scimed, Inc., Maple Grove, MN (US)

(72) Inventors: Christopher Benning, Hopkinton, MA (US); Paul Aquilino, Walpole, MA (US); John Hutchins, North Attleboro, MA (US); Scott Tupper, Pascoag, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/249,951

(22) Filed: Jan. 17, 2019

(65) Prior Publication Data

US 2019/0142248 A1    May 16, 2019

Related U.S. Application Data

(63) Continuation of application No. 13/682,548, filed on Nov. 20, 2012, now abandoned.

(60) Provisional application No. 61/562,142, filed on Nov. 21, 2011.

(51) Int. Cl.
| | |
|---|---|
| *A61B 1/00* | (2006.01) |
| *A61B 1/06* | (2006.01) |
| *A61B 1/05* | (2006.01) |
| *A61B 1/12* | (2006.01) |
| *A61B 1/07* | (2006.01) |

(52) U.S. Cl.
CPC ...... *A61B 1/00137* (2013.01); *A61B 1/00096* (2013.01); *A61B 1/00101* (2013.01); *A61B 1/05* (2013.01); *A61B 1/0676* (2013.01); *A61B 1/128* (2013.01); *A61B 1/07* (2013.01); *F04C 2270/041* (2013.01)

(58) Field of Classification Search
None
See application file for complete search history.

(56) References Cited

U.S. PATENT DOCUMENTS

| 2001/0025174 A1 | 9/2001 | Daniel et al. |
| 2006/0111612 A1 | 5/2006 | Matsumoto |

(Continued)

FOREIGN PATENT DOCUMENTS

| EP | 1 955 642 A1 | 3/2008 |
| JP | 2001-8892 A | 1/2001 |

(Continued)

OTHER PUBLICATIONS

International Search Report for corresponding International Application No. PCT/US2012/066143, dated Jan. 30, 2013 (4 pages).

*Primary Examiner* — Timothy J Neal
(74) *Attorney, Agent, or Firm* — Bookoff McAndrews, PLLC (57) ABSTRACT

This invention may be directed to an endoscopic device. The endoscopic device comprising an elongate member having a distal end, and a cap positioned at the distal end. The cap may have a proximal end and a distal end. The proximal end may define at least one recess that does not extend through the cap to the distal end of the cap. The endoscopic device may further include at least one illumination device disposed in the at least one recess.

20 Claims, 8 Drawing Sheets

(56) References Cited

U.S. PATENT DOCUMENTS

| | | | |
|---|---|---|---|
| 2006/0199999 A1* | 9/2006 | Ikeda | A61B 1/00149 600/141 |
| 2007/0066869 A1* | 3/2007 | Hoffman | A61B 1/00135 600/121 |
| 2007/0249907 A1 | 10/2007 | Boulais et al. | |
| 2008/0021274 A1 | 1/2008 | Bayer et al. | |
| 2009/0048486 A1* | 2/2009 | Surti | A61B 1/0008 600/127 |
| 2010/0188493 A1 | 7/2010 | Kanzaki et al. | |
| 2010/0231783 A1* | 9/2010 | Bueler | G02B 3/14 348/347 |
| 2010/0286475 A1 | 11/2010 | Robertson | |

FOREIGN PATENT DOCUMENTS

| | | |
|---|---|---|
| JP | 2403-190091 A | 7/2003 |
| JP | 2007-21084 A | 2/2007 |
| WO | 2005/094665 A2 | 10/2005 |
| WO | 2010/129324 A2 | 11/2010 |

\* cited by examiner

ENDOSCOPIC SYSTEM FOR OPTIMIZED VISUALIZATION

CROSS-REFERENCE TO RELATED APPLICATIONS

This is a continuation application of pending U.S. Nonprovisional application Ser. No. 13/682,548, filed Nov. 20, 2012, which claims the benefit of priority from U.S. Provisional Application No. 61/562,142, filed Nov. 21, 2011, the entireties of each of which is herein incorporated by reference in its entirety.

FIELD OF THE INVENTION

Embodiments of the present disclosure relate to an endoscopic system. In particular, exemplary embodiments of the present disclosure relate to endoscopic devices of the endoscopic system for optimized visualization. Embodiments of the present disclosure also cover methods of using such devices.

BACKGROUND OF THE INVENTION

An endoscope is a flexible device introduced into the body for diagnostic and/or therapeutic purposes. Typically, these devices are inserted into the body through an opening (a natural opening or an incision), and are delivered to a work site inside the body through a body cavity. Generally, such devices include an illumination device to illuminate a field of view at the work site, and an imaging device to allow a surgeon to see the work site from outside the body and remotely operate the endoscope to perform a desired diagnostic/therapeutic procedure at the work site.

In reusable endoscopes, a diffusing lens may be provided with the Illumination device at the distal end of the endoscope to project light evenly over the entire visualization field. Due to the differences in proximities, and other light reflecting characteristics of different locations within the field of view of the work site (such as, for example, differences in reflectivity of muscle and tissue), these different locations may appear to be Illuminated differently. For instance, some of these locations may appear to be oversaturated with light while other locations may appear to be insufficiently illuminated. The variation in illumination may make visualization of the work site difficult, and may therefore be undesirable. With small bore endoscopes, the cost of implementing a diffusing lens for even distribution of light may be high. While this cost may be less of an issue with reusable endoscopes where the cost can be amortized due to repeated usage, this cost may be prohibitively high in the case of disposable endoscopes. Therefore, the present disclosure is directed to systems and methods to optimize visualization by controlling distribution of light in a field of view within the body from outside the body.

SUMMARY OF THE INVENTION

Embodiments of the present disclosure are directed to endoscopic systems, devices, and methods that obviate one or more of the limitations discussed above.

One embodiment of the disclosure is directed to an endoscopic device. The endoscopic device may include an elongate member having a distal end, and a cap positioned at the distal end. The cap may have a proximal end and a distal end. The proximal end may define at least one recess that does not extend through the cap to the distal end of the cap. The endoscopic device may also include at least one illumination device disposed in the at least one recess.

In various embodiments, the endoscopic device may include one or more of the following additional features: wherein the cap includes a translucent material; wherein the cap is filled with material configured to scatter light; wherein the at least one illumination device is an optical fiber; wherein the cap includes an opening extending from the proximal end of the cap to the distal end of the cap, and wherein a lighting device is disposed in the opening; wherein the lighting device is an optic fiber configured to provide down field illumination; further including an imaging device at the distal end of the elongate member; wherein the imaging device is received in a viewing port of the cap; and wherein the cap includes a rim that extends over the distal end of the elongate member.

Another embodiment of the disclosure is directed to a cap for an endoscopic device. The cap may include a body defining a lumen extending through the body from a proximal end of the body to a distal end of the body. The cap may further include at least one recess extending into the body from a proximal end to a position within the body.

In various embodiments, the cap may include one or more of the following additional features: wherein the body is filled with material so as to diffuse light; wherein the body is translucent; wherein the at least one recess is arranged at a periphery of the body; wherein the at least one recess has a diameter that is smaller than a diameter of the lumen; further including at least one cooling channel; further including a viewing port extending from the proximal end of the body to the distal end of the body.

Another embodiment of the disclosure is directed to a method of using an endoscopic device. The method may include inserting a distal portion of an endoscopic device into a body. The endoscopic device may include an elongate member having a distal end. A cap may be positioned at the distal end of the elongate member. The cap may have a proximal end and a distal end. The proximal end may define one or more recesses that do not extend through the cap to the distal end. One or more illumination devices may be disposed in the one or more recesses. The method may also include positioning the distal portion of the endoscopic device proximate a work site within the body and activating the one or more illumination devices to provide diffused illumination at the worksite.

In various embodiments, the method may include one or more of the following additional features: wherein the endoscopic device further includes a lighting device disposed in an opening of the cap to provide down field illumination; wherein the cap is filled with material configured to scatter light; wherein the cap is translucent; wherein the endoscopic device further includes an imaging device, and further including activating the imaging device to view the work site.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

The accompanying drawings, which are incorporated in and constitute a part of this specification, illustrate embodiments of the disclosure and together with the description, serve to explain the principles of the disclosure.

DESCRIPTION OF THE EMBODIMENTS

Reference will now be made in detail to exemplary embodiments of the disclosure, examples of which are illustrated in the accompanying drawings. Whenever possible, the same reference numbers will be used throughout the drawings to refer to same or like parts.

Figure 1:
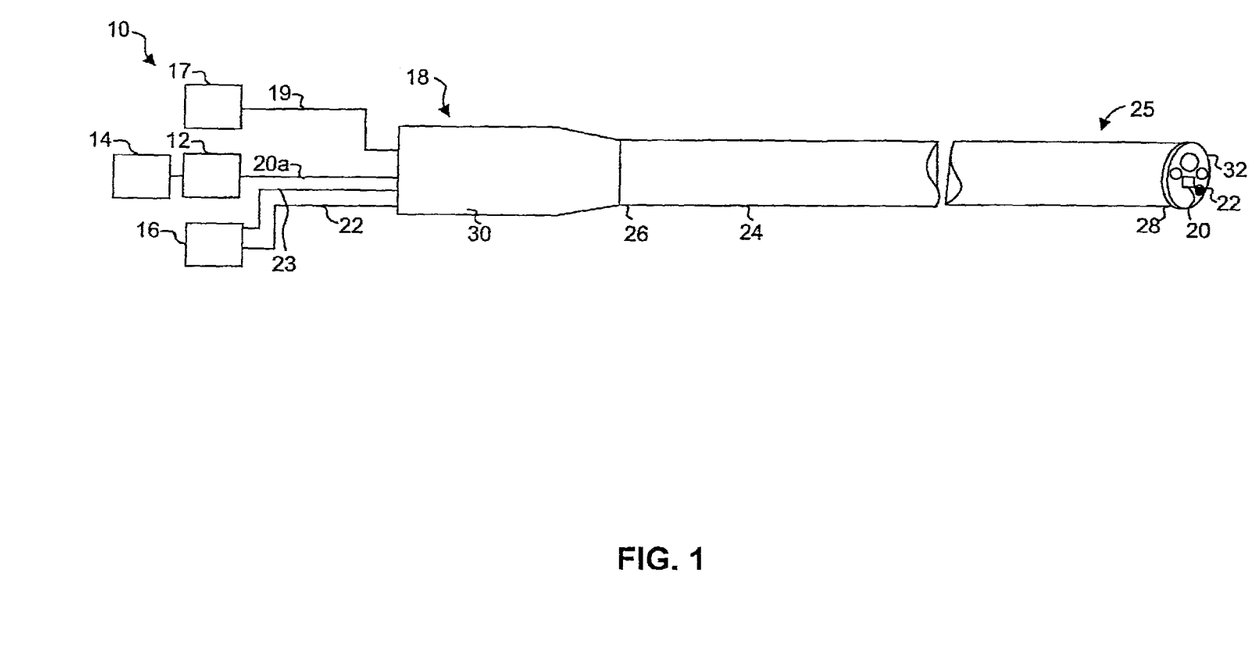
FIG. 1 illustrates an endoscopic system including an endoscopic device, according to an embodiment of the disclosure.

FIG. 1 illustrates an exemplary endoscopic system 10 and related components. The exemplary endoscopic system 10 may be used for therapeutic and/or diagnostic endoscopic procedures. The phrase "endoscopic procedure" is broadly used to indicate any medical procedure that may be performed by inserting an endoscope, laparoscope, guide tube, catheter, or any such medical device into the body through any natural, surgical, percutaneous, or other opening in the body. The term "endoscopic system" is also used broadly to include all components and systems that may be used for the endoscopic procedure. In the exemplary embodiment, the components of endoscopic system 10 may include a control device 12, a display 14 which may be connected to control device 12, an illumination control system 16, a fluid and/or vacuum source 17, and an endoscopic device 18. Control device 12 and fluid source 17 may be connected to endoscopic device 18 by way of a wire or a cable 20a, and fluid conduit 19, respectively. Illumination control system 16 may be connected to endoscopic device 18 by way of a lighting device 22 and one or more illumination devices 23. Endoscopic device 18 may have a distal portion 25 configured to be positioned at a worksite in a body cavity.

Endoscopic device 18 may include an elongate member 24 having a proximal end 26 and a distal end 28. For purposes of this disclosure, "proximal" refers to the end closer to the device operator during use, and "distal" refers to the end further from the device operator during use. A handle portion 30 may be disposed at proximal end 26 of elongate member 24, and a cap 32 may be positioned at distal end 28 of elongate member 24. Handle portion 30 may be any known, suitable handle. Cap 32 may provide diffused illumination at the worksite.

Figure 2:
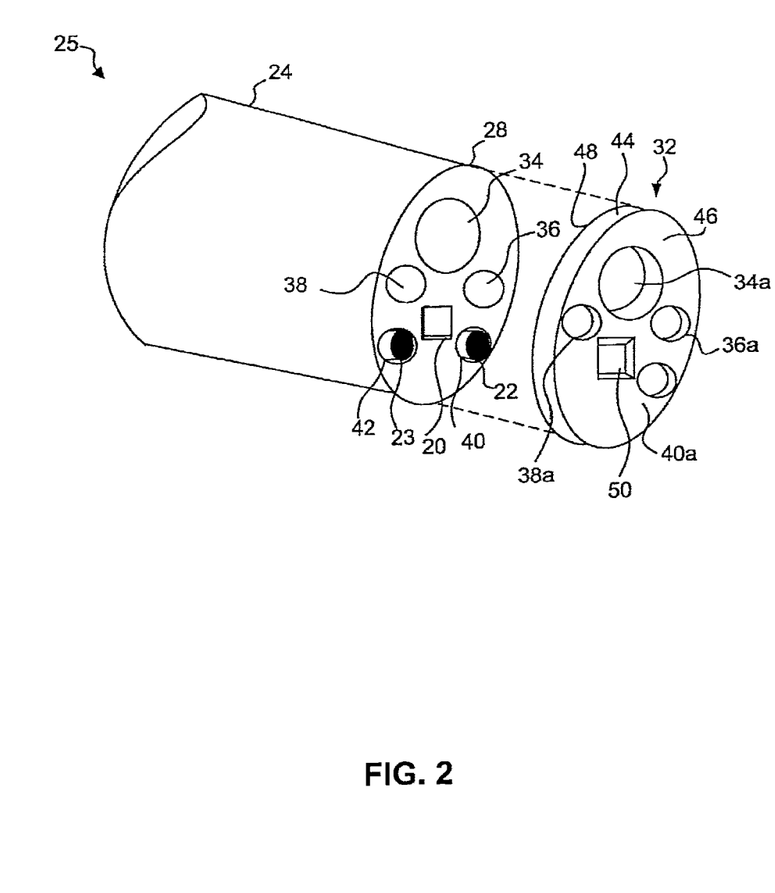
FIG. 2 is an exploded view of a distal portion of the endoscopic device having a cap, according to a first embodiment of the disclosure.

FIG. 2 is an exploded view of distal portion 25 of endoscopic device 18. Elongate member 24 may be a flexible tube, made from any suitable biocompatible material known to one of ordinary skilled in the art having sufficient flexibility to traverse a body cavity. Such materials may include, but are not limited to, rubber, silicon, synthetic plastic, stainless steel, metal-polymer composites, and metal alloys of nickel, titanium, copper cobalt, vanadium, chromium, and iron. In one embodiment, the material forming elongate member 24 may be a superelastic material such as nitinol, which is a nickel-titanium alloy. In some embodiments, elongate member 24 may include layers of different materials and reinforcements. Elongate member 24 may have any cross-sectional shape and/or configuration and may be any desired dimension that can be received in a body cavity. In some embodiments, elongate member 24 may be made of, or coated with, a polymeric or lubricious material to enable endoscopic device 18 to pass through a body cavity with ease. It is contemplated that endoscopic device and/or elongate member 24 may be steerable and may have areas of different flexibility or stiffness (e.g., to promote steerability).

Elongate member 24 may include one or more lumens extending proximally from distal end 28 to proximal end 26. It is to be understood that lumens may have any size, cross-sectional area, shape, and/or configuration. In some embodiments, lumens may be extruded in elongate member 24. Lumens may provide access to instruments at proximal end 26 that may aid in performing desire medical procedures at a worksite within a body cavity. These lumens may include one or more of, among others, a working lumen 34, an irrigation lumen 36, and an aspiration lumen 38. In addition, elongate member 24 may include a first lumen 40 and a second lumen 42. First lumen 40 may be configured to receive lighting device 22, and second lumen 42 may be configured to receive illumination device 23.

An imaging device 20 may be embedded into elongated member 24 and mounted on distal end 28 of elongate member 24. Imaging device 20 may include a camera, lens, digital imaging chip, or other image receiving device, which may transmit signals using wire or cable 20a (fiber optic or another type of cable) within elongate member 24. In some embodiments, image signals from imaging device 20 may be processed by control device 14 before being directed to display device 16. It is also contemplated that, in some systems, control device 14 may also direct a control signal to imaging device 20 to control various aspects of its operation. In some embodiments, in addition to, or in place of imaging device 20 fixed to distal end 28, a second imaging device may be delivered to distal end 28 through working lumen 34 of elongate member 24. In those embodiments, the second imaging device may be movable relative to elongate member 24.

Cap 32 may be positioned at distal end 28 of elongate member 24, and coupled to distal end 28 of elongate member 24. In some embodiments, cap 32 may be integral with distal end 28 of elongate member 24, while in other embodiments, cap 32 may be a part separate from distal end 28 of elongate member 24. In those embodiments, cap 32 may be secured to distal end 28 of elongate member 24 by, for example, an interference fit, a snap fit, threads, or any other securing device known to those skilled in the art. Cap 32 may have any useful shape to aid with procedures, delivering of light, and/or diffusing light. For example, cap 32 may be cylindrical, bulbous, and may have angled surfaces. An outer rim 44 of cap 32 may extend over distal end 28 of elongate member 24. In some embodiments, rim 44 may be rounded or have beveled edges to provide increased patient comfort and to reduce the chance of injury to the patient. Cap 32 may be made of a translucent plastic material by any suitable method including, for example, injection molding, machining, or lithography. In one embodiment, cap 32 may be made an acrylic polymer filled with TiO2. The acrylic material may create a scatter effect to light that enters cap 32. Scattering may be facilitated in any number of other ways known in the art, including fillers, opaque materials, bubbles, diffusing or opaque coatings, or surface treatments or patterns.

Figure 3A:
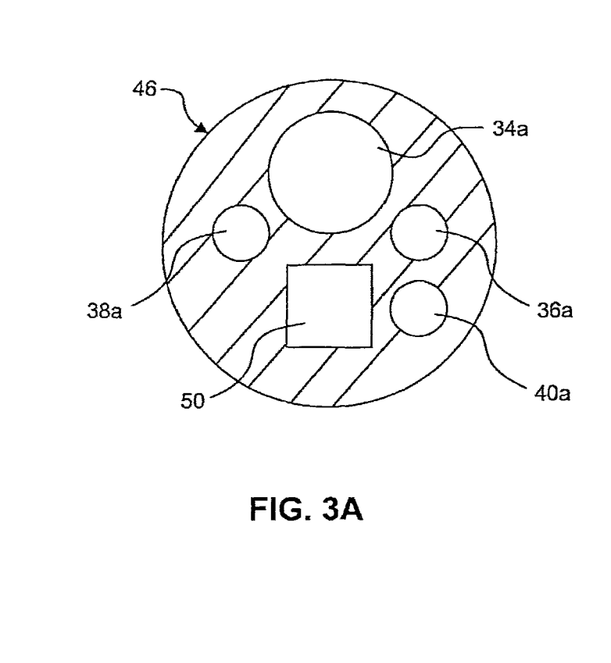
FIG. 3A is a distal end view of the cap, according to a first embodiment of the disclosure.
Figure 3B:
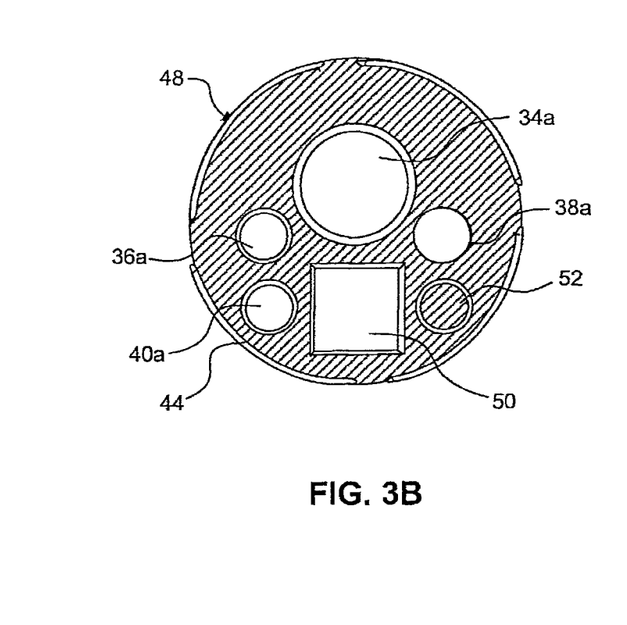
FIG. 3B is a proximal end view of the cap, according to a first embodiment of this disclosure.

Cap 32 may have a distal end 46 and a proximal end 48. FIG. 3A illustrates distal end 46 of cap 32, and FIG. 3B illustrates proximal end 48 of cap 32. As shown in FIGS. 3A and 3B, cap 32 may define a plurality of ports extending through proximal end 48 and distal end 46 of cap 32. Ports may have any size, cross-sectional area, shape, and/or configuration. In the exemplary embodiment, ports may include one or more of, among others, a working port 34a, an irrigation port 36a, an aspiration port 38a, a viewing port 50, and a light port 40a. Proximal end 48 of cap 32 may also include a recess 52 formed in cap 32. Recess 52 may terminate within cap 32 and may not extend through to distal end 46.

Figure 4A:
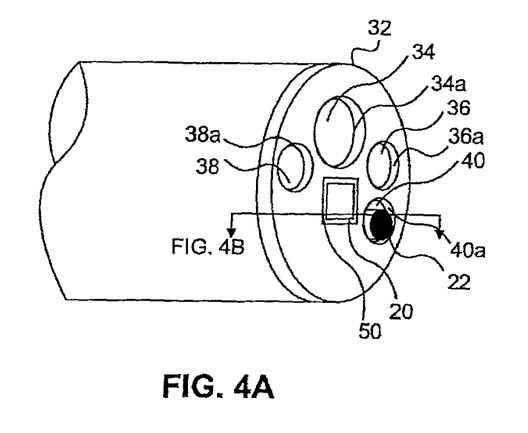
FIG. 4A is a perspective view of the distal portion of the endoscopic device, according to a first embodiment of the disclosure.
Figure 4B:
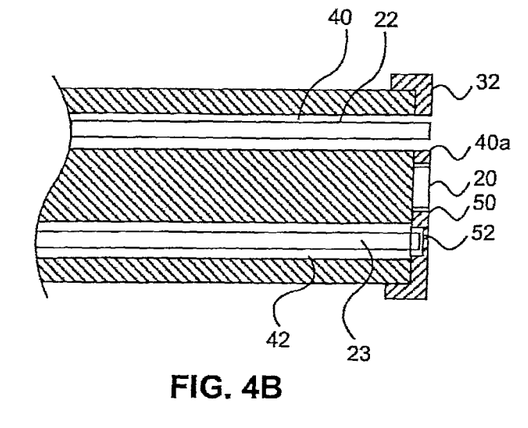
FIG. 4B is a longitudinal cross-section of the distal portion, according to a first embodiment of the disclosure.

Referring to FIGS. 4A and 4B, working port 34a may be in communication with working lumen 34, and may be configured to deliver an endoscopic instrument or device (not shown) to the work site. The endoscopic instrument may include any tool that is configured to perform a desired function at the work site while being remotely controlled by an actuation device from outside the body. The endoscopic instrument may be configured as an end effector attached at a distal end of an endoscopic instrument. Irrigation port 36a may be in communication with irrigation lumen 36, and may be configured to deliver fluids from fluid source 17 to the worksite. Aspiration port 38a may be in communication with aspiration lumen 38, and may be configured to facilitate suction and/or fluid flow at the worksite.

Viewing port 50 may be aligned with imaging device 20. Imaging device 20 may be adjacent to, flush with, or protruding from viewing port 50. In some embodiments, imaging device 20 may move relative to viewing portion 50. Lighting device 22 may be disposed within first lumen 40 of elongate member 24, and may be adjacent to, flush with, or protruding from light port 40a of cap 32. In some embodiments, lighting device 22 may be moveable relative to first lumen 40 and light port 40a of cap 32. Illumination device 23 may be disposed within second lumen 42 of elongate member 24. Illumination device 23 may terminate in recess 52 of cap 32 (FIG. 4B). Illumination device 23 may be movable relative to second lumen 42 so that illumination device 23 may be positioned at the distal end 28 of elongate member 24 or in recess 52 of cap 32. It is contemplated that cap 32 may accommodate multiple light sources, imaging source, etc.

In some embodiments, lighting device 22 and/or illumination device 23 may comprise (glass or plastic) fiber optic cables, which extend from distal end 28 of elongate member-to proximal end 26 of elongate member 24. In other embodiments, lighting device 22 or illumination device 23 may comprise a light source such as, for example, a bulb, an LED, or a light guide. In yet other embodiments, lighting may be provided as a combination of sources (e.g., illumination device may comprise a light fiber and lighting device may comprise an LED). While a single lighting device 22 and illumination device 23 are discussed, it is contemplated that any number of lighting or illumination devices may be used.

Lighting device 22 and illumination device 23 may direct light to cap 32 from illumination control system 16 (FIG. 1). Illumination control system 16 may include light source, control electronics, and associated control algorithms that operate cooperatively to modulate the amount of light directed to lighting device 22 and illumination device 23. In one embodiment, illumination control system 16 may include a single light source with individual lenses, irises, and/or filters to modulate the amount of light directed to lighting device 22 and illumination device 23. Any optical arrangement known in the art may be used to split the light from the single light source into multiple beams having different characteristics and direct each beam through the individual illumination devices. In other embodiments, illumination control system 16 may include different light sources for lighting device 22 and illumination device 23. The light sources may be, for example, a LED, a Xenon lamp, or another known light source.

In some embodiments, illumination control system 16 may include a control algorithm to adjust the illumination at the work site automatically. This control algorithm may include software codes that analyze the images from imaging device 20 and automatically control the intensity of light in each of lighting device 22 and illumination device 23. In some embodiments, the illumination control system 16 may be configured to "learn" from each illumination adjustment operation and improve over time.

In applications involving disposable endoscopes, illumination control system 16 may form the capital equipment that may be used along with a disposable endoscope. Since the illumination control system 16 may be reused with different disposable endoscopes, the sensitivity of cost of the illumination control system 16 to the application may be low.

Figure 5:
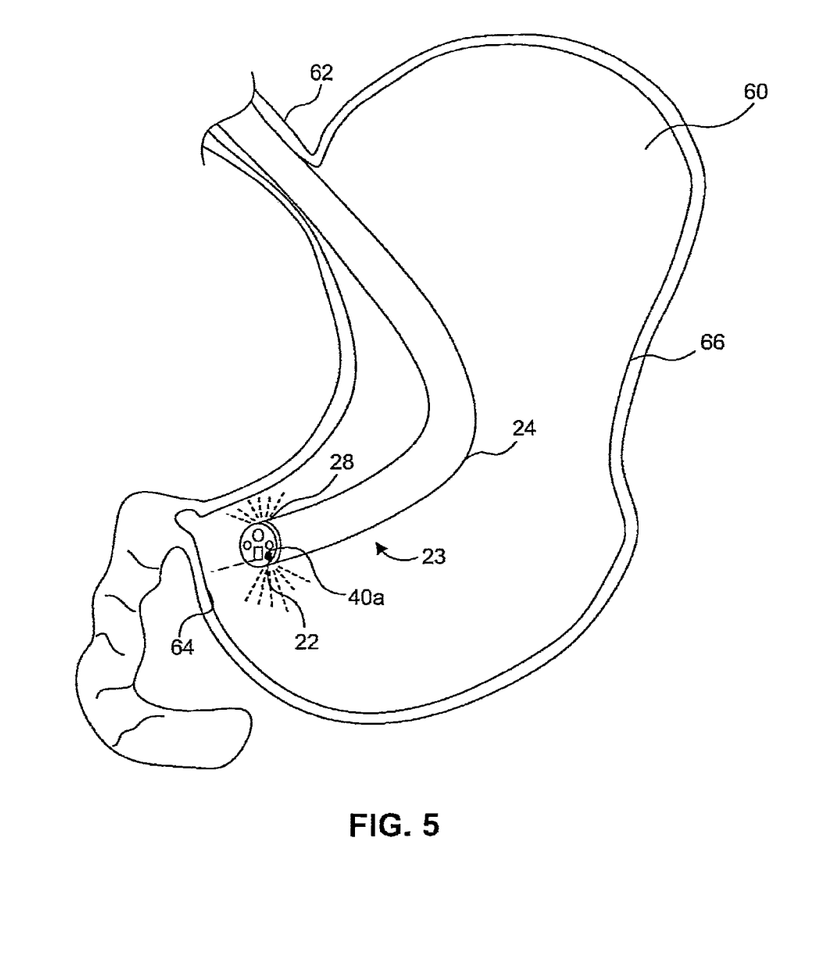
FIG. 5 is a schematic view of an embodiment of the endoscopic device during an exemplary endoscopic procedure.

Referring to FIG. 5, endoscopic device 18 may be inserted into a body cavity and positioned adjacent a work site. In the illustrated embodiment, endoscopic device 18 may be inserted into stomach 60 through the esophagus 62, and positioned in stomach 60 such that distal end 23 of endoscopic device 18 may be positioned proximate a work site 64 on stomach wall 66. A proximal end 26 (not shown in FIG. 5) of elongate member 24 of endoscopic device 18 may extend out of the body of the patient and may be controlled to perform the desired operations at the distal end 28 of elongate member 24. It should be emphasized that the medical procedure illustrated in FIG. 5 is exemplary only, and that endoscopes of the current disclosure may be applied to any endoscopic application known in the art.

After distal portion 25 is disposed at worksite 64, imaging device 20 may be activated so that a user may view work site 64. Lighting device 22, positioned in illumination port 40a, may then be activated to emit a distally directed path of light and provide distal field illumination. Illumination device 23 (not shown in FIG. 5) may be activated to emit light into cap 32. Cap 32 may made from a translucent material such as, for example, an acrylic filled with TiO2 that may scatter light as light enters cap 32, causing cap 32 to glow. In this manner, cap 32 may provide diffused, near field illumination.

It is contemplated that, in all embodiments, cap 32 may further comprise cooling channels in addition to or in place of irrigation lumen 36 and aspiration lumen 38 to help offset any heat created by lighting device 22, illumination device 23, and/or imaging device 20. Fluid may be directed through the cooling channels in cap 32 and out may be expelled either distally of cap 32 or at proximal end 26 of elongate member 24.

A user may control light directed through lighting device 22 and illumination device 23 independently via illumination control system 16 to optimize visualization. A user may also independently control the characteristics of the light directed to each of lighting device 22 and illumination device 23. The characteristics may include intensity, wavelength, polarization, color, frequency, phase or any other characteristic that can vary the level of illumination directed through each of lighting device 22 and illumination device 23.

Figure 6:
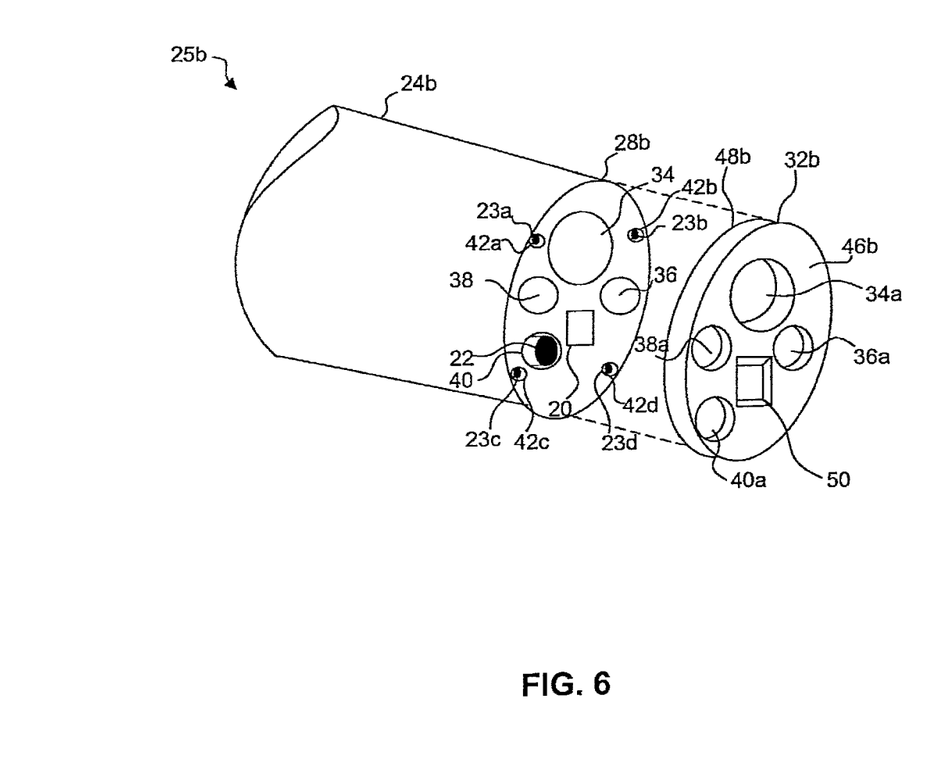
FIG. 6 is an exploded view of a distal portion of the endoscopic device having a cap, according to a second embodiment of the disclosure.

FIG. 6 illustrates a distal portion 25b of endoscopic device 18, in accordance with another embodiment of the present disclosure. Elongate member 24b may include one or more lumens extending proximally through distal end 28b and its proximal end (not shown). Like FIG. 2, these lumens may include one or more of, among others, a working lumen 34, an irrigation lumen 36, an aspiration lumen 38, and a first lumen 40. In addition, elongate member 24b may include one or more second lumens 42. In the exemplary embodiment, elongate member 24b may include four second lumens 42a, 42b, 42c, and 42d that receive four illumination devices 23a, 23b, 23c, and 23d, respectively. It is contemplated that a greater or lesser number of illumination devices 23 may be provided.

Cap 32b may be positioned at distal end 28b of elongate member 24b, and extend distally from distal end 28b of elongate member 24b. Cap 32b may be made of a translucent plastic material by any suitable method including, for example, injection molding or machining. In one embodiment, cap 32b may be made an acrylic polymer filled with $TiO_2$. The acrylic material may create a scatter effect to light that enters cap 32b. Scattering, however, may be facilitated in any number of other ways known in the art, including fillers, opaque materials, bubbles, diffusing or opaque coatings, surface treatments or patterns.

Figure 7A:
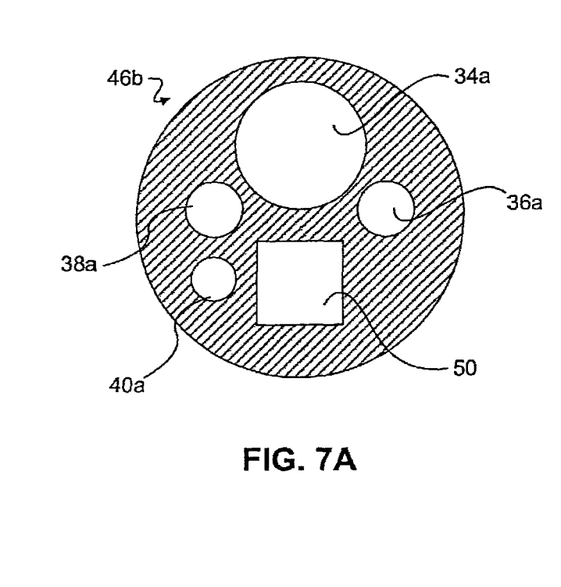
FIG. 7A is a distal end view of the cap, according to a second embodiment of the disclosure.
Figure 7B:
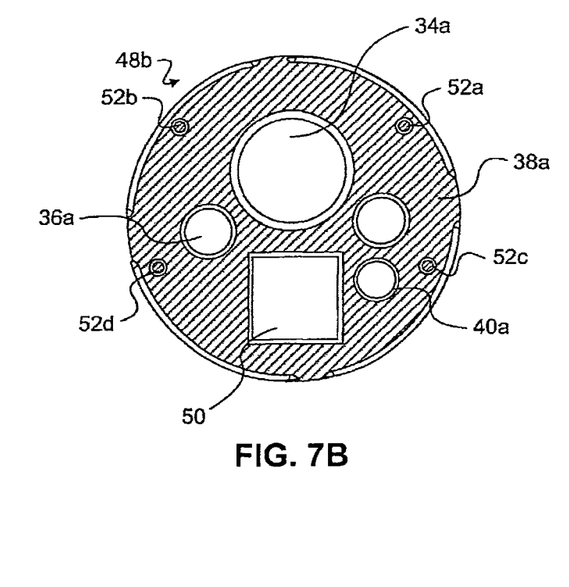
FIG. 7B is a proximal end view of the cap, according to a second embodiment of the disclosure.

Cap 32b may have a distal end 46b and a proximal end 48b. FIG. 7A illustrates distal end 46b of cap 32b, and FIG. 7B illustrates proximal end 48b of cap 32b. As shown in FIGS. 7A and 7B, cap 32b may define a plurality of ports extending through proximal end 48b and distal end 46b of cap 32b. Like cap 32, cap 32b may include a working port 34a, an irrigation port 36a, an aspiration port 38a, a viewing port 50, and a light port 40a. In this embodiment, however, proximal end 48b of cap 32b may have one or more recesses 52 formed in cap 32 that terminate within cap 32 and do not extend through to distal end 46. In the exemplary embodiment, cap 32b has four recesses 52a, 52b, 52c, and 52d that are arranged on the periphery of cap 32. Recesses 52a, 52b, 52c, and 52 may form any arrangement on proximal end 48b of cap 32b. It is to be understood that the number of recesses may correspond to the number of illumination devices.

Figure 8A:
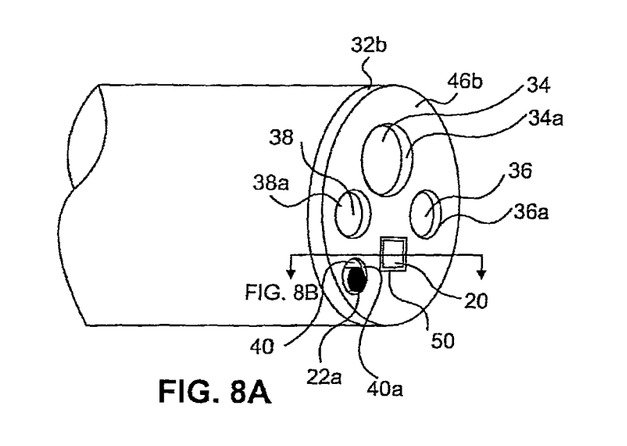
FIG. 8A is a perspective view of the distal portion of the endoscopic device, according to a second embodiment of the disclosure.
Figure 8B:
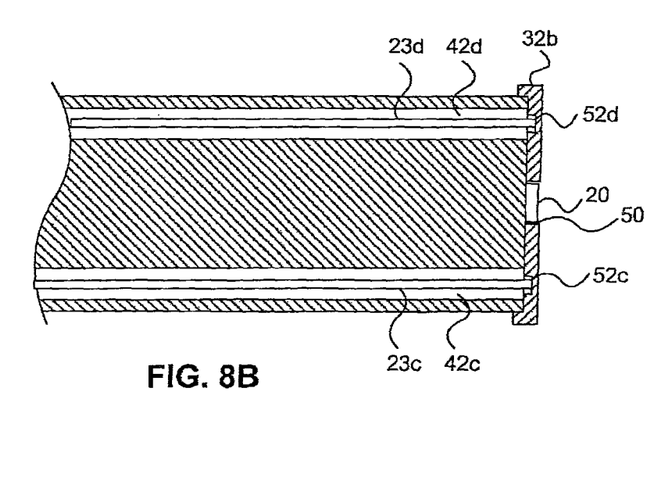
FIG. 8B is a longitudinal cross-section of the distal portion, according to a second embodiment of the disclosure.

Referring to FIGS. 8A and 8B, lighting device 22 may be disposed within first lumen 40 of elongate member 24b and may be adjacent to, flush with, or protruding from light port 40a. Lighting device 22 may be configured to emit a distally directed path of light to provide down field illumination. Illumination devices 23a, 23b, 23c, and 23d may be disposed within second lumens 42a, 42b, 42c, and 42d of elongate member 24b, and may terminate in recesses 52a, 52b, 52c, and 52d formed in cap 32b. Illumination devices 23a, 23b, 23c, and 23d may be configured to emit light into cap 32b. In this manner, cap 32b may provide diffused, near field illumination.

In this embodiment, lighting device 22 and illumination devices 23a, 23b, 23c, and 23d may be optic fibers. Illumination devices 23a, 23b, 23c, and 23d may be smaller fibers and lighting device 22 may be a larger optic fiber. Characteristics of the light emitted by illumination devices 23a, 23b, 23c, and 23d may be individually varied by illumination control system 16. For instance, the intensity of the light emitted by each of illumination devices 23a, 23b, 23c, and 23d may be varied individually by illumination control system 16. In other embodiments, the characteristic of light that is varied by illumination control system 16 may include a wavelength of the light directed through each of illumination devices 23a, 23b, 23c, and 23d.

In some additional and/or alternative embodiments, lighting device 22 may be operatively coupled with an adjustable diffusing lens or other adjustable lens membranes. In these embodiments, a characteristic of the light emitted by lighting device 22 may be changed by selectively activating the diffusing lens or lens membrane associated with that lighting device 22. The diffusing lens or lens membrane may be selectively activated by any means, such as, for example, a pressure may be applied to the lens membrane to change its optical properties, and therefore, a characteristic of light passing through the membrane. A pressure may be applied to the lens membrane by applying an electric current to the membrane.

In some embodiments, the lenses may be independently controlled to aim light at or away from a particular point, direct, focus, obscure, and/or change a characteristic of the light (for example, frequency, etc.). In some embodiments, a lens or another optical member associated with an illumination device may be biased to provide more (or less) illumination to a region of work site 64 illuminated by that lighting device 22. In some embodiments, the illumination control system 16 may vary a cant or tilt of an optic fiber (or another illumination device) relative to a longitudinal axis of the endoscopic device 18 to vary a characteristic of light delivered to work site 64 through that fiber. The cant of the fiber optic may be changed by advancing or retracting wedges or other positioning mechanisms associated with that fiber. Alternatively, the cap may have angled ports to direct light device outward or inward. In some embodiments, one or more light sensors could be used in addition to, or as, cameras. These light sensors may assist in automatically or manually adjusting the illumination effect. In these embodiments, the cap may have any number of lumens and recesses.

It is contemplated that in any of the embodiments described above, the cap may, alternatively, opaque and may include one or more portions that are transparent or translucent. For example, the cap may be entirely opaque and include one or more transparent or translucent lenses or windows formed therein relatively adjacent one or more of the lumens in the elongate member. For example, it is contemplated that the cap may include a transparent or translucent lens or window within the recess such that light emitted from an illumination device disposed within the recess of the cap may pass through the lens or window and thus through cap and may illuminate a work space. Alternatively, the cap may be translucent and/or may include material configured to scatter light, and may additionally include one or more transparent portions, e.g., lenses or windows to selectively allow emitted light to pass through the cap.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An endoscopic device comprising:
    a member having a distal end;
    a plurality of illumination devices for emitting light from the distal end of the member; and
    a cap at the distal end of the member, wherein an entirety of the cap is translucent, and wherein the cap includes:
        a wall having a proximally-facing surface and a distally-facing surface,
        a recess in the wall, the recess having an open end at the proximally-facing surface of the wall and a closed end between the proximally-facing and distally-facing surfaces of the wall, wherein the recess receives light emitted from a distal end of a first illumination device of the plurality of illumination devices, and wherein the light emitted from the distal end of the first illumination device passes through a translucent material of the cap before being emitted from the cap at the distal end of the member, and
        a light port in the wall, the light port having open ends at the proximally-facing and distally-facing surfaces of the wall, wherein the light port receives light emitted from a second illumination device of the plurality of illumination devices, and wherein the light emitted from the distal end of the second illumination device is emitted from the distal end of the member via the open end of the light port at the distally-facing surface.

2. The endoscopic device of claim 1, wherein the light emitted from the distal end of the first illumination device is diffused by the cap.

3. The endoscopic device of claim 1, wherein the light emitted from the distal end of the second illumination device is emitted from the light port without passing through any material but air.

4. The endoscopic device of claim 1, wherein the cap further includes a viewing port in the wall for receiving an imaging device, wherein the recess is on a first side of the viewing port, and wherein the light port is on a second side of the viewing port, the first and second sides being opposite sides of the viewing port.

5. The endoscopic device of claim 1, further including one or more additional illumination devices of the plurality of illumination devices for emitting light from the distal end of the member, wherein the cap further includes one or more additional recesses, and wherein each of the one or more additional recesses receives light emitted from a distal end of one of the one or more additional illumination devices.

6. The endoscopic device of claim 5, wherein each of the one or more additional recesses has an open end at the proximally-facing surface of the wall and a closed end between the proximally-facing and distally-facing surfaces of the wall, and wherein the light emitted from the one or more additional illumination devices passes through a translucent material of the cap before being emitted from the cap at the distal end of the member.

7. The endoscopic device of claim 6, wherein each of the one or more additional recesses is disposed on a periphery of the cap.

8. The endoscopic device of claim 5, wherein a wavelength emitted by each of the plurality of illumination devices and each of the additional illumination devices is individually adjustable.

9. The endoscopic device of claim 1, further including an imaging device and a controller operatively coupled to the plurality of illumination devices, wherein the controller analyzes image data from the imaging device and automatically adjusts an intensity of each of the plurality of illumination devices based on the analysis.

10. The endoscopic device of claim 1, wherein a complete cross-section of the wall including the closed end consists of a uniform material.

11. The endoscopic device of claim 1, wherein the cap includes a rim extending around a perimeter of the proximal-facing surface of the wall and projecting proximally from the wall, wherein the rim receives the distal end of the member and positions the distal end of the member adjacent the proximal-facing surface of the wall, and wherein the rim extends over and radially outward of the distal end of the member.

12. An endoscopic device comprising:
    a member having a distal end;
    an illumination device for emitting light from the distal end of the member;
    an imaging device at the distal end of the member; and
    a cap formed entirely from a translucent material and positioned at the distal end of the member, the cap having:
        a wall having a proximally-facing surface and a distally-facing surface,
        a recess in the wall, the recess having an open end at the proximally-facing surface of the wall and a closed end between the proximally-facing and distally-facing surfaces of the wall, wherein the recess receives light emitted from a distal end of the illumination device, and wherein the light emitted from the distal end of the illumination device passes through a material forming the wall before being emitted from the cap at the distal end of the member, and
        a viewing port in the wall, the viewing port having open ends at the proximally-facing and distally-facing surfaces of the wall, wherein the imaging device is aligned with the viewing port.

13. The endoscopic device of claim 12, wherein the illumination device is a first illumination device, and wherein the cap has a light port in the wall, the light port having open ends at the proximally-facing and distally-facing surfaces of the wall, wherein the light port receives light emitted from a second illumination device, and wherein the light emitted from a distal end of the second illumination device is emitted from the distal end of the member via the open end of the light port at the distally-facing surface.

14. The endoscopic device of claim 13, further including a controller operatively coupled to the first and second illumination devices, wherein the controller independently controls the first and second illumination devices to adjust one or more characteristics of light emitted from the distal end of the member.

15. The endoscopic device of claim 13, wherein the light emitted from the distal end of the second illumination device is emitted from the light port without passing through the material forming the wall.

16. The endoscopic device of claim 12, wherein a complete cross-section of the wall including the closed end consists of a uniform composition of the translucent material.

17. An endoscopic device comprising:
a member having a distal end;
a plurality of illumination devices for emitting light from the distal end of the member; and
an entirely translucent cap at the distal end of the member, wherein the cap includes:
a wall having a proximally-facing surface and a distally-facing surface,
a first recess in the wall, the first recess having an open end at the proximally-facing surface of the wall and a closed end between the proximally-facing and distally-facing surfaces of the wall, wherein the first recess receives light emitted from a distal end of a first illumination device of the plurality of illumination devices, and wherein the light emitted from the distal end of the first illumination device passes through material forming the wall before being emitted from the cap at the distal end of the member, and
a second recess in the wall, the second recess having an open end at the proximally-facing surface of the wall and a closed end between the proximally-facing and distally-facing surfaces of the wall, wherein the second recess receives light emitted from a distal end of a second illumination device of the plurality of illumination devices, and wherein the light emitted from the distal end of the second illumination device passes through the material forming the wall before being emitted from the cap at the distal end of the member.

18. The endoscopic device of claim 17, further comprising an imaging device at the distal end of the member, wherein the cap further includes a viewing port in the wall, the viewing port having open ends at the proximally-facing and distally-facing surfaces of the wall, and wherein the imaging device is aligned with the viewing port.

19. The endoscopic device of claim 17, wherein a complete cross-section of the wall including the closed end of the first recess consists of a uniform material.

20. The endoscopic device of claim 17, wherein each of the first recess and the second recess is disposed on a periphery of the cap.

* * * * *